United States Patent
Saitou et al.

(10) Patent No.: US 9,222,129 B2
(45) Date of Patent: Dec. 29, 2015

(54) METHOD FOR AMPLIFICATION OF NUCLEOTIDE SEQUENCE

(75) Inventors: Mitinori Saitou, Hyogo (JP); Kazuki Kurimoto, Hyogo (JP); Yukihiro Yabuta, Hyogo (JP); Yasuhide Ohinata, Hyogo (JP)

(73) Assignee: RIKEN, Saitama (JP)

( * ) Notice: Subject to any disclaimer, the term of this patent is extended or adjusted under 35 U.S.C. 154(b) by 2139 days.

(21) Appl. No.: 11/884,084

(22) PCT Filed: Feb. 10, 2006

(86) PCT No.: PCT/JP2006/302360
§ 371 (c)(1), (2), (4) Date: Jun. 10, 2008

(87) PCT Pub. No.: WO2006/085616
PCT Pub. Date: Aug. 17, 2006

(65) Prior Publication Data
US 2009/0291852 A1 Nov. 26, 2009

(30) Foreign Application Priority Data
Feb. 10, 2005 (JP) .................... 2005-034573

(51) Int. Cl.
*C12Q 1/68* (2006.01)
*C40B 30/00* (2006.01)

(52) U.S. Cl.
CPC ..................... *C12Q 1/686* (2013.01)

(58) Field of Classification Search
None
See application file for complete search history.

(56) References Cited

U.S. PATENT DOCUMENTS

2003/0017482 A1  1/2003  Godfrey et al.
2004/0086906 A1  5/2004  Takiguchi

FOREIGN PATENT DOCUMENTS

| WO | WO99/25873 | * | 5/1999 | ............... C12Q 1/68 |
| WO | WO 99/25873 A1 | | 5/1999 | |
| WO | WO 02/052031 A2 | | 7/2002 | |
| WO | WO 03/020979 A1 | | 3/2003 | |

OTHER PUBLICATIONS

Kurimoto et al. (Nucleic Acids Research, 2006, 34(5):e42, p. 1-17.*
Frohman et al. (PNAS, 1988, 85(2):8998-9002).*
Prashar et al. (PNAS, 1996, 93, p. 659-663).*
Craggs et al. (J Virol. Meth. 2001, 94, p. 111-120).*
DeRisi et al. (Nature, 1996, vol. 14, p. 457-460).*
Frohman, Methods of Enzymology, 1993, 218, p. 340-356.*
Belyavsky et al. (Nucleic Acids Research, 1989, 17(8):2919-2932).*

(Continued)

*Primary Examiner* — Stephanie K Mummert
(74) *Attorney, Agent, or Firm* — Sterne, Kessler, Goldstein & Fox P.L.L.C.

(57) ABSTRACT

A method for amplification of a nucleotide sequence characterized by performing PCR amplification using mRNA isolated from a biological sample as a template and using a first primer comprising a poly(T) sequence and an additional nucleotide sequence X thereto and a second primer comprising a poly(T) sequence and an additional nucleotide sequence Y thereto, provided that the nucleotide sequences X and Y in the first and second primers, respectively, have different sequences from each other.

17 Claims, 5 Drawing Sheets

(56) References Cited

OTHER PUBLICATIONS

Rajeevan, M.S. et al., "Global amplification of sense RNA: a novel method to replicate and archive mRNA for gene expression analysis," *Genomics* 82:491-497, Elsevier Inc. (2003).

Supplementary European Search Report for EP 06713503.8, European Patent Office, Munich, Germany, mailed Jun. 4, 2009.

Brady. G., et al., "Representative in Vitro cDNA Amplification From Individual Hemopoietic Cells and Colonies," *Methods Mol. Cell. Biol*. 2:17-25, Wiley-Liss, Inc. (1990).

Iscove, N.N., et al., "Representation is faithfully preserved in global cDNA amplified exponentially from sub-picogram quantities of mRNA," *Nat. Biotechnol*. 20:940-943, Nature Publishing Group (2002).

Kamme, F., et al., "Single-Cell Microarray Analysis in Hippocampus CA1: Demonstration and Validation of Cellular Heterogeneity," *J. Neurosci*. 23:3607-3615, Society for Neuroscience (2003).

Tietjen, I., et al., "Single-Cell Transcriptional Analysis of Neuronal Progenitors," *Neuron* 38:161-175, Cell Press (2003).

Tang, F. et al., "Development and applications of single-cell transcriptome analysis," *Nature. Methods Supplement*. 8:S6-S11, Nature Publishing Group (2011).

\* cited by examiner (a)

(b)

SEQUENCE LISTING

<160> NUMBER OF SEQ ID NOS: 4

<210> SEQ ID NO 1
<211> LENGTH: 48
<212> TYPE: DNA
<213> ORGANISM: Artificial Sequence
<220> FEATURE:

```
<223> OTHER INFORMATION: Description of Artificial Sequence: primer

<400> SEQUENCE: 1
atatggatcc ggcgcgccgt cgactttttt tttttttttt tttttttt                48

<210> SEQ ID NO 2
<211> LENGTH: 48
<212> TYPE: DNA
<213> ORGANISM: Artificial Sequence
<220> FEATURE:
<223> OTHER INFORMATION: Description of Artificial Sequence: primer

<400> SEQUENCE: 2
atatctcgag ggcgcgccgg atccttttttt tttttttttt tttttttt               48

<210> SEQ ID NO 3
<211> LENGTH: 63
<212> TYPE: DNA
<213> ORGANISM: Artificial Sequence
<220> FEATURE:
<223> OTHER INFORMATION: Description of Artificial Sequence: primer

<400> SEQUENCE: 3
ggccagtgaa ttgtaatacg actcactata gggaggcgga tatggatccg gcgcgccgtc   60
gac                                                                 63

<210> SEQ ID NO 4
<211> LENGTH: 24
<212> TYPE: DNA
<213> ORGANISM: Artificial Sequence
<220> FEATURE:
<223> OTHER INFORMATION: Description of Artificial Sequence: primer

<400> SEQUENCE: 4
tatagaattc gcggccgctc gcga                                          24
```

METHOD FOR AMPLIFICATION OF NUCLEOTIDE SEQUENCE

TECHNICAL FIELD

The present invention relates to a method for amplification of a nucleotide sequence for enabling a quantitative microarray analysis, particularly to a method for amplification of a nucleotide sequence for enabling a quantitative microarray analysis using a small number of cells, preferably at a single cell level.

BACKGROUND ART

Life phenomena are a system that is realized by complex interaction among many gene products, and it is an essential as a starting point to accurately grasp the expression dynamics of each gene product for understanding the true nature of the life phenomena. Microarrays are actively used as means for the systematic analysis of gene expression. A microarray analysis is a method in which thousands to tens of thousands of oligonucleotide spots are formed on a support such as a slide glass, a target prepared from RNA derived from cells or tissues to be analyzed are hybridized, and the amount of transcription of each gene is comprehensively measured using the intensity of hybrid formation obtained as an index. This method is useful for efficiently and quantitatively measuring the dynamic behavior of all genes involved in living organisms, whereby the method provides gene expression information in various life phenomena and may be a first step for expanding the method to effective applications in a medical, food industry or substance production field.

A series of oligonucleotide microarray GeneChip (trade name: manufactured by Affymetrix, Inc.) is able to comprehensively and quantitatively measure a gene expression level and becomes almost mainstream. In this method, cDNA is prepared first by reverse transcription of total mRNAs derived from cells or tissues, labeled cRNA (antisense strand) is synthesized by in-vitro transcription reactions using T7 RNA polymerase, and the synthesized cRNA is hybridized on the array. However, 1,000 to 100,000 cells are necessary for extractin the total mRNA to prepare a target.

Since a trace amount of cells comprising an extremely small number of cells are responsible for crucial functions in the generation process of multicellular organisms including human and in nerve cells, blood cells, somatic stem cells and cancer cells, it seems essential to ultimately analyze one cell, or at a single cell level. As an important point of an analysis at the single cell level, it is necessary to amplify the target nucleotide sequence to a level capable of applying to the microarray analysis for a quantitative microarray analysis. It is also necessary to amplify the nucleotide sequence while a relative relation of a gene expression level in the single cell is maintained as much as possible.

A method for synthesizing cDNAs from a quite minute amount of mRNA at the single cell level and for amplifying the cDNAs while the relative relation of gene expression level is maintained had been first proposed by G. Brady et al. in 1990, and has been improved thereafter (Non-patent Documents 1 and 2). Microarray experiments carried out by labeling the cDNAs amplified by this method with fluorescent reagents have been reported in 2003 (Non-patent Document 3). However, these technologies have some defects to be described below, and quantitative a microarray analysis at the single cell level has not been practically used yet.

(1) Distortion of Relative Relation of Gene Expression Level by Usual PCR Method In a PCR method, DNA is exponentially amplified by doubling a template and further doubling the template. Accordingly, a quite small difference of amplification efficiency among different gene products finally causes a multi-fold difference, to largely distort the relative relation of the gene expression level. This is serious for the gene products whose expression level is relatively small, and is a dominant cause for relatively large decrease of detection sensitivity of such a gene product. Such distortion of the relative relation of the gene expression level in the amplification process by the usual PCR method is referred to a "systematic error".

(2) Variation of Gene Expression Level in Amplification Process

Random errors in the amplification process are also exponentially amplified due to exponential amplification characteristics of the PCR method. A small error caused in each step of the amplification process finally generates a severalfold difference. Thereafter, this is a crucial factor for reducing reliability when the expression level of each gene product is estimated after amplification. This is a so-called random error of the expression level of each gene in the amplification process.

In recent years, there is reported, in order to overcome the defects of the PCR method, a method for addition of a 3'-end T7 promoter when synthesizing a primary chain of cDNA from a minute amount of mRNA at the single cell level (in case of synthesis of a primary cDNA chain) to perform amplification (linear amplification) by an in vitro transcription reaction (Non-patent Document 4). A kit taking advantage of this principle has been commercialized (sales agent: EPICENTRE Biotechnologies). However, a work for extracting RNAs from a single cell is necessary for the oligonucleotide microarray experiments for amplifying a minute amount of mRNA at the single cell level by using this kit while the relative relation of the gene expression level is maintained. However, there is not practical to extract and purify a minute amount of RNA at this level, and it cannot be denied that a low copy mRNA may be lost in this work. In addition, since the amplification efficiency of the nucleotide sequence by linear amplification is extremely inferior to the amplification efficiency by the PCR method, the amount of the amplification products to be obtained is small. Further, since only one microarray experiment can be performed in one amplification experiment and the amplification product is inevitably labeled RNA in the linear amplification, and preservation of the sample is difficult as compared with DNA samples. It is inconvenient that a reverse transcription reaction is necessary again before gene-specific PCR for confirming whether amplification has been succeeded or not because the amplification product is labeled RNA. Furthermore, since high level of skill is necessary for complicated experimental works in which synthesis and purification of RNA are repeated, this method seems to be not suitable for an analysis at an actual single cell level.

Non-patent Document 1: Brady, G., M. Barbara et al. (1990), "Representative in vitro cDNA amplification from individual henopoietic cells and colonies", Methods Molec. Cell. Biol. 2 (17-25)

Non-patent Document 2: Iscove, N. N., M. Barbara, et al., (2002), "Representation is faithfully preserved in global cDNA amplified exponentially from sub-picogram quantities of mRNA", Nat Biotechnol 20(9): 940-3

Non-patent Document 3: Tietjen, I., J. M. Rihel, et al. (2003), "Single-cell transcriptional analysis of neuronal progenitors", Neuron 38(2): 161-75

Non-patent Document 4: Kamme et al., "Single-Cell Microarray Analysis in Hippocampus CA1: Demonstration and Validation of Cellular Heterogeneity", The Journal of Neuroscience, May 1, 2003, 23(9):3607

DISCLOSURE OF THE INVENTION

Problems to be Solved by the Invention

Since the methods for amplification of a nucleotide sequence so far have not attained a level sufficient for applying to standard protocols of most of oligonucleotide microarray experiments including the method presented by Affymetrix, Inc., more efficient and simple methods for amplification of a nucleotide sequence are desired.

Means for Solving the Problems

A PCR method may be conveniently used as an amplification method in terms of efficiency and simplicity when an amplification product is applied to a series of oligonucleotide array GeneChip manufactured by Affymetrix, Inc. However, the above-mentioned serious errors that are exponentially increased by PCR amplification should be avoided.

Accordingly, in the present invention, by the following method, cDNA is synthesized from a minute amount of RNA at a single cell level and cDNA is amplified while the relative relation of the gene expression level is maintained as much as possible, to enable a quantitative microarray analysis.

The present invention relates to
(1) a method for preparing a group of nucleic acids comprising amplification products retaining a relative relation of the gene expression level in a biological sample, including the steps of:

(a) preparing a primary cDNA chain by reverse transcription using mRNA isolated from a biological sample, specifically cells of eukaryotic organisms, preferably one to several cells, more preferably one cell, and using a first primer comprising a poly(T) sequence and an additional nucleotide sequence X thereto, preferably a first primer comprising a nucleotide sequence represented by SEQ ID No. 1, preferably preparing a primary cDNA chain by a reverse transcription reaction for 5 to 10 minutes, or preparing a primary cDNA chain having an approximately uniform length;

(b) inactivating the remaining first primer, preferably inactivating the remaining first primer by decomposition with exonuclease I, after the reaction in step (a);

(c) subjecting the primary cDNA chain obtained in step (a) to a poly(A) tailing reaction followed by preparing secondary double-stranded DNA chain, using the poly(A) tailing reaction product as a template and using a second primer comprising a poly(T) sequence and an additional nucleotide sequence Y thereto, preferably a second primer comprising a nucleotide sequence represented by SEQ ID No. 2, wherein the nucleotide sequences X and Y in the first and second primers, respectively, have different sequences from each other;

(d) adding the first primer, and performing PCR amplification, preferably amplifying for 10 to 30 cycles, more preferably dividing the secondary double-stranded DNA chain obtained in step (c) into 3 to 10 portions followed by amplifying each portion by PCR and collecting each amplification product together, more preferably performing PCR amplification at an annealing temperature close to Tm of the primer; and (e) performing PCR amplification using primer set (1) or (2) below, preferable amplifying for 4 to 10 cycles, more preferably performing PCR amplification at an annealing temperature close to Tm of the primer:

(1) a primer set comprising a combination of a third primer comprising the additional nucleotide sequence X and a promoter sequence linked to a 5'-end of the nucleotide sequence X, and the second primer, or (2) a primer set comprising a combination of the third primer comprising the additional nucleotide sequence Y and a promoter sequence linked to a 5'-end of the nucleotide sequence Y, preferably a third primer having a nucleotide sequence represented by SEQ ID No. 3, and the first primer; and preferably, the method further including (f) a step for preparing a group of nucleic acids comprising labeled RNA by applying RNA polymerase and labeled nucleotide triphosphate to the group of nucleic acids obtained in step (e).

The present invention relates to a group of nucleic acids prepared by the method of the present invention comprising amplification products retaining the relative relation of the gene expression level in a biological sample, wherein the amplification product has an approximately uniform length.

The present invention relates to a quantitative microarray analysis method for applying the group of nucleic acids to a microarray.

The present invention relates to a primer pair comprising a nucleic acid molecule having the nucleotide sequence represented by SEQ ID No. 1, a nucleic acid molecule having the nucleotide sequence represented by SEQ ID No. 2, a nucleic acid molecule having the nucleotide sequence represented by SEQ ID No. 3, and the nucleic acid molecule having the nucleotide sequence represented by SEQ ID No. 1, and the nucleic acid molecule having the nucleotide sequence represented by SEQ ID No. 2.

The present invention relates to
(2) a method for amplification of a nucleotide sequence including the steps of:

(a) preparing a primary cDNA chain by reverse transcription using mRNA isolated from a biological sample, specifically cells of eukaryotic organisms, preferably one to several cells, more preferably one cell, and using a first primer comprising a poly(T) sequence and an additional nucleotide sequence X thereto, preferably a first primer comprising a nucleotide sequence represented by SEQ ID No. 1, preferably preparing a primary cDNA chain by a reverse transcription reaction for 5 to 10 minutes, or preparing a primary cDNA chain having an approximately uniform length;

(b) inactivating the remaining first primer, preferably inactivating the remaining first primer by decomposition with exonuclease I, after the reaction in step (a);

(c) subjecting primary cDNA chain obtained in step (a) to a poly(A) tailing reaction followed by preparing secondary double-stranded DNA chain, using the poly(A) tailing reaction product as a template and using a second primer comprising a poly(T) sequence and an additional nucleotide sequence Y thereto, preferably a second primer comprising a nucleotide sequence represented by SEQ ID No. 2, wherein the nucleotide sequences X and Y in the first and second primers, respectively, have different sequences from each other;

(d) adding the first primer, and performing PCR amplification, preferably amplifying for 10 to 30 cycles, more preferably dividing the secondary double-stranded DNA chain obtained in step (c) into 3 to 10 portions followed by amplifying each portion by PCR and collecting each amplification product together, more preferably performing PCR amplification at an annealing temperature close to Tm of the primer; and (e) performing PCR amplification using primer set (1) or (2) below, preferable amplifying for 4 to 10 cycles of PCR amplification, more preferably amplifying at an annealing temperature close to Tm of the primer, (1) a primer set comprising a combination of a third primer comprising the nucleotide sequence X and a promoter sequence linked to a 5'-end of the nucleotide sequence X, and the second primer, or (2) a primer set comprising a combination of the third primer comprising the nucleotide sequence Y and a promoter sequence linked to a 5'-end of the nucleotide sequence Y, preferably the third primer having a nucleotide sequence represented by SEQ ID No. 3, and the first primer; preferably, the method further including (f) a step for preparing a group of nucleic acids comprising labeled RNA by applying RNA polymerase and labeled nucleotide triphosphate to the group of nucleic acids obtained in step (e); and more preferably, the method in which a nucleotide sequence contains an amplification product retaining a relative relation of a gene expression level in the biological sample.

The present invention relates to (3) a method for preparing a nucleic acid library retaining a relative relation of the gene expression level in a biological sample including the steps of:

(a) preparing a primary cDNA chain by reverse transcription using mRNA isolated from a biological sample, specifically cells of eukaryotic organisms, preferably one to several cells, more preferably one cell, and using a first primer comprising a poly(T) sequence and an additional nucleotide sequence X thereto, preferably a first primer comprising a nucleotide sequence represented by SEQ ID No. 1, preferably preparing a primary cDNA chain by a reverse transcription reaction for 5 to 10 minutes, or preparing a primary cDNA chain having an approximately uniform length;

(b) inactivating the remaining first primer, preferably inactivating the remaining first primer by decomposition with exonuclease I, after the reaction in step (a);

(c) subjecting primary cDNA chain obtained in step (a) to a poly(A) tailing reaction followed by preparing secondary double-stranded DNA chain, using the poly(A) tailing reaction product as a template, by using a second primer comprising poly(T) sequence and an additional nucleotide sequence X thereto, preferably a second primer comprising a nucleotide sequence represented by SEQ ID No. 2, wherein the nucleotide sequences X and Y in the first and second primers, respectively, have different sequences from each other;

(d) adding the first primer, and performing PCR amplification, preferably amplifying for 10 to 30 cycles, more preferably dividing the secondary double-stranded DNA chain obtained in step (c) into 3 to 10 portions followed by amplifying each portion by PCR and collecting each amplification product together, more preferably performing PCR amplification at an annealing temperature close to Tm of the primer; and (e) performing PCR amplification using primer set (1) or (2) below, preferable amplifying for 4 to 10 cycles of PCR amplification, more preferably amplifying at an annealing temperature close to Tm of the primer:

(1) a primer set comprising a combination of a third primer comprising the nucleotide sequence X and a promoter sequence linked to a 5' end of the nucleotide sequence X, and the second primer; or (2) a primer set comprising a combination of the third primer comprising the nucleotide sequence Y and a promoter sequence linked to a 5' end of the nucleotide sequence Y, preferably a third primer having a nucleotide sequence represented by SEQ ID No. 3, and the first primer; and preferably, the method further including (f) a step for preparing a group of nucleic acids comprising labeled RNA by applying RNA polymerase and labeled nucleotide triphosphate to the group of nucleic acids obtained in step (e).

The present invention relates to (4) a kit for preparing a group of cDNAs for applying to a microarray, including;

(a) a first primer comprising a poly(T) sequence and an additional nucleotide sequence X thereto, preferably a first primer comprising a nucleotide sequence represented by SEQ ID No. 1, for preparing a primary cDNA chain from mRNA isolated from a biological sample, specifically cells of eukaryotic organisms, preferably one to several cells, more preferably one cell;

(b) a reagent for inactivating the first primer, preferably exonuclease I;

(c) a second primer comprising a poly(T) sequence and an additional nucleotide sequence Y thereto, preferably a second primer comprising a nucleotide sequence represented by SEQ ID No. 2, wherein the nucleotide sequences X and Y in the first and second primers, respectively, have different sequences from each other; and (d) a primer set (1) or (2) below:

(1) a primer set comprising a combination of a third primer comprising the nucleotide sequence X and a promoter sequence linked to a 5'-end of the nucleotide sequence X, and the second primer, or (2) a primer set comprising a combination of the third primer comprising the nucleotide sequence Y and a promoter sequence linked to a 5'-end of the nucleotide sequence Y, preferably a third primer having the nucleotide sequence represented by SEQ ID No. 3, and the first primer; and preferably, the kit includes a group of cDNAs comprising an amplification product retaining a relative relation of the gene expression level in a biological sample.

Effects of the Present Invention

The present invention provides a highly reliable quantitative amplification technology of a minute amount of cDNA by a simple PCR method directly applicable to an oligonucleotide microarray. The method of the present invention permits template cDNA in an amount sufficient for microarray experiments to be synthesized and amplified from a single cell in one day's experiment. A conventional method and the method of the present invention are compared by real-time PCR experiments using several gene products as probes, and it has been confirmed that systematic errors and random errors are remarkably improved without suspicion. It has been also confirmed in the microarray experiment using the method of the present invention that a quantitative analysis at a single cell level was possible with further improved reproducibility as compared with the conventional method

BEST MODE FOR CARRYING OUT THE PRESENT INVENTION

(1) Method for Preparing a Group of Nucleic Acids Comprising Amplification Products that Retain Relative Relation of a Gene Expression Level in Biological Samples The present invention provides a method for preparing a group of nucleic acids that retains a relative relation of gene expression levels in a biological samples, and the group of nucleic acids obtained by the method.

The "amplification products that retain the relative relation of the gene expression level in a biological samples" as used in the present invention refers to the amplification products in which the constitution of the entire gene products in the biological sample is almost retained, or refer to the amplification products ensuring a level that may be applied to a standard protocol of the oligonucleotide microarray experiment, or a production amount of the level applicable to a the microarray analysis.

The "biological sample" as used in the present invention refers to cells of eukaryotic organisms such as the biological species having a poly(A) sequence at a 3'-end of mRNA, for example animals including mammals such as human and mouse, plants, fungi and protista. Specifically, the present invention is expected to be applied to nerve cells, blood cells, somatic stem cells or cancer cells as a biological sample.

While the number of the cells as the biological sample is not particularly limited, the present invention may be applied to 100 cells or less, tens of cells and one to several cells, and ultimately one cell level, in terms of the fact that amplification with good reproducibility is possible while the relative relation of the gene expression level in the biological sample is maintained.

The "quantitative microarray analysis" refers to a microarray analysis that is able to display the gene expression level in the biological sample by reflecting the expression level on, for example, the intensity of labeling such as fluorescence intensity. In the microarray analysis, gene fragments (probes) are immobilized on a small size glass substrate in a high density, fluorescence labeled RNAs (targets) for analyzing gene expression are hybridized with the probes, and the gene expression level is measured based on the fluorescence intensity. More comprehensive analysis of gene expression is possible by increasing the number of the gene fragments immobilized as the probes.

The outline of the method of the present invention is as follows. Primary cDNA chain are produced with a first primer, unreacted primers of the first primer are inactivated, a poly(A) is added with TdT, secondary strains are produced with a second primer, and the first primer is again added, and PCR amplification is performed. Then, the amplification products are further amplified using a third primer and the second primer. Thereafter, by-products at the lower molecular weight side that are obviously not derived from mRNAs are optionally removed.

Figure 1:
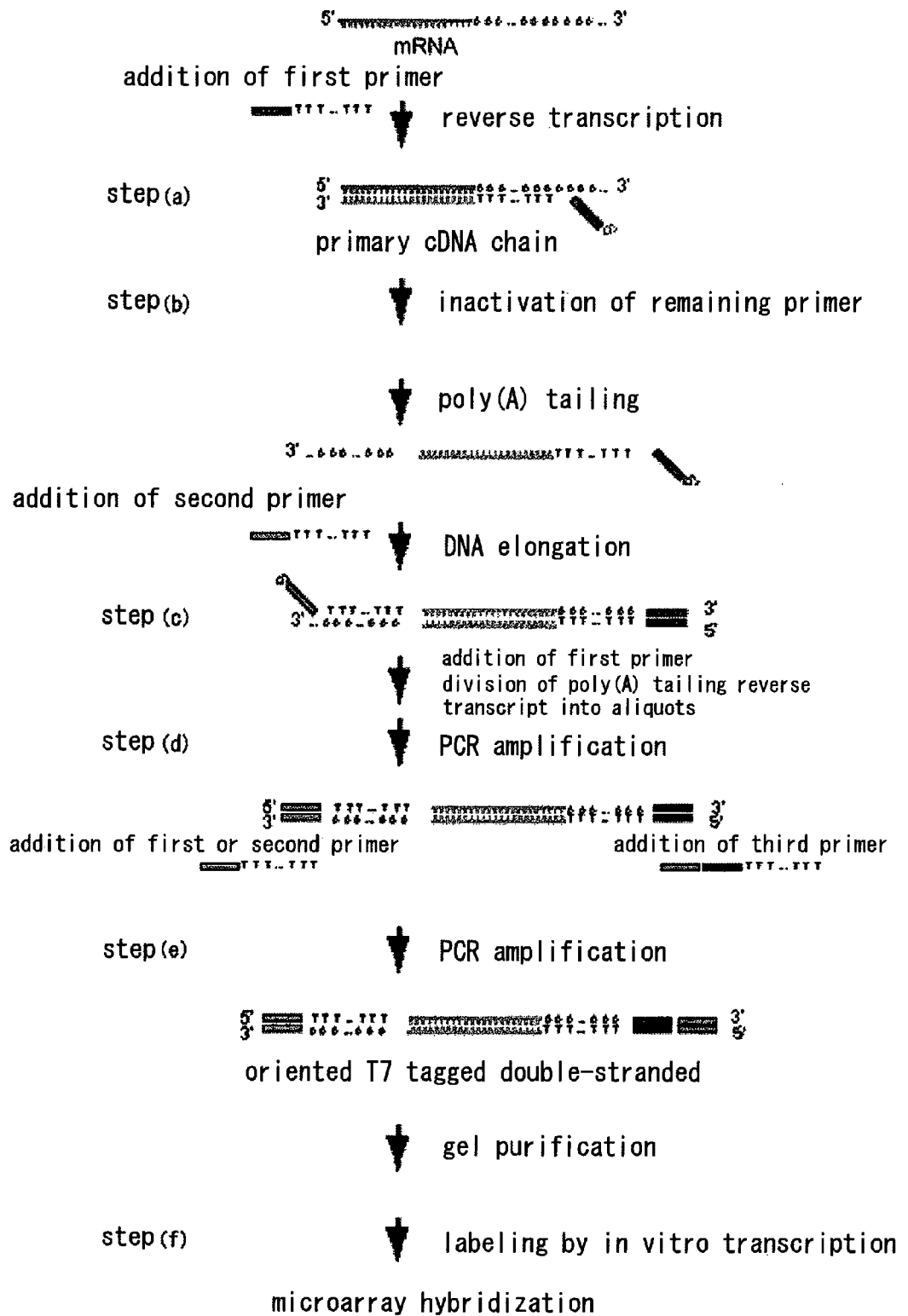
FIG. 1 is a chart for describing the method for amplification of a nucleotide sequence according to the present invention.

The outline of the method of the present invention is shown in FIG. 1. FIG. 1 is only a description of one example of the methods of the present invention, and the present invention may be implemented by those skilled in the art by addition of appropriate modifications. Each step of the method of the present invention will be described in detail below with reference to FIG. 1.

(a) Preparation of Primary cDNA Chain

A primary cDNA chain is prepared using the first primer comprising a poly(T) sequence and an additional nucleotide sequence X thereto by reverse transcription using mRNA isolated from a biological sample as a template. The time for the reverse transcription reaction is preferably shortened in the range form 5 to 10 minutes, more preferably to about 5 minutes, so that amplification efficiency in the PCR reaction thereafter does not dependent on the length of the template cDNA. This permits a primary cDNA chain having a uniform length with respect to mRNAs having longer total length to be synthesized. "Approximately uniform length of the primary cDNA chain" refers to the primary cDNA chain having a uniform length with respect to mRNAs having longer total length, and presence of shorter cDNAs is not excluded.

(b) Inactivation of Remaining First Primer

In step (b), the remaining first primer is removed by decomposition or other methods after the reaction in step (a). Specifically, the remaining primer may be decomposed with exonuclease I or exonuclease T. Alternatively, the remaining primer may be inactivated by modifying the 3'-end of the primer with alkali phosphatase and the like.

In the conventional method, by-products generated in the amplification process account for 30% or more (for example, see Non-patent Document 2). The inventors have found that the by-product is formed by amplification of the remaining primer via a non-intended path during the synthesis of primary cDNA chain, and the amount of the by-product formed may be suppressed in minimum by inactivating the remaining primer.

(c) Poly(A) Tailing Reaction, and Preparation of Secondary Double-Stranded DNA Chain Using a Second Primer The primary cDNA chain obtained in step (a) is subjected to a poly(A) tailing reaction, and secondary double-stranded DNA chain is prepared using a second primer comprising poly(T) sequence and an additional nucleotide sequence Y thereto.

While the second primer used in this step has a different nucleotide sequence from that of the first primer used in step (a), the second primer has a certain identity with the first primer and does not contain any promoter sequences.

It is impossible to synthesize only cRNA by addition of T7 promoter in the conventional amplification technology of a quite minute amount of cDNA, since the same primer is used for the 3'-end and 5'-end of cDNA. When synthesizing RNA labeled from both ends (3'- and 5'-ends) or directly labeled double-stranded cDNA is hybridized on an array, the RNA or cDNA is not always quantitatively hybridized to the oligonucleotide on the array since sense strands and antisense strands are hybridized from each other. Accordingly, excellent reproducibility and quantitativity of the oligonucleotide array may be severely spoiled.

It has been found through trials and errors that primer sets comprising different sequences from each other but resembling from each other may be more efficiently amplified.

The first and second primers will be described in more detail below.

The nucleotide sequences X and Y in the first primer used in step (a) (the poly(T) sequence and the additional nucleotide sequence X thereto) and the second primer used in step (b) (the poly(T) sequence and the additional nucleotide sequence Y thereto) have different sequences from each other. Using different primers at the 3'-end and 5'-end of cDNA permits PCR amplification thereafter to have directionality that may discriminate the 3'-end from the 5'-end. Therefore, T7 promoter can be added to only 3' end of cDNA in the step thereafter. Both systematic errors and random errors are remarkably increased when a primer comprising T7 promoter is used at the beginning of amplification. Accordingly, the nucleotide sequences X and Y are required to contain no promoter sequences.

The common sequence of the additional nucleotide sequences X and Y is selected so that Tm of the common sequence of the additional nucleotide sequences X and Y is lower than Tm of the first primer and Tm of the second primer, and so that Tm of the common sequence is apart from Tm of the first primer and Tm of the second primer as much as possible. This permits undesirable cross-annealing by which the first and second primers are annealed at different cites by annealing in the PCR reaction thereafter to be prevented. In other words, Tm of the common sequence is selected so that it does not exceed the annealing temperature for annealing the first and second primers thereafter. Tm denotes a temperature when one half of DNA molecules are annealed with complimentary strands. The annealing temperature is set at a temperature that enables the primers to form pairs, and is usually lower than Tm of the primer.

The nucleotide sequences of the first primer and second primer have preferably 77% or more, more preferably 78% or more and further preferably 80±1%, and most preferably 79% identity from each other. The upper limit of identity of the sequence is the upper limit percentage (%) where Tm of the common sequence of both primers does not exceed the annealing temperature as described above. The nucleotide sequences of the first primer and second primer may be defined so that the additional nucleotide sequences X and Y have preferably 55% or more, more preferably 57% or more and further preferably 60±2% identity from each other. The upper limit of identity is the upper limit percentage (%) where Tm of the common sequence of the additional nucleotide sequences X and Y does not exceed the annealing temperature in the PCR reaction.

The additional nucleotide sequences X and Y in the first and second primers to be used preferably have respective palindromic sequences. Specifically, since almost all the restriction enzyme cites such as AscI, BamHI, SalI and XhoI cites as well as EcoRI, EcoRIV, NruI and NotI cites have the palindromic sequence, the sequences X and Y may have these sequences. Accordingly, specific examples of the first and second primers include a primer pair of the nucleic acid molecule having the nucleotide sequence represented by SEQ ID No. 1 and the nucleic acid molecule having the nucleotide sequence represented by SEQ ID No. 2.

The identity in the nucleotide sequences of the first and second primers is based on the following experimental examples in which retention of the relative relation of the gene expression level was not so good by amplification.

Example 1

When T7 promoter is used as the 3'-end primer and a sequence in which the sequence of T7 promoter from the 5'-end to the 3'-end is reversed (T7-reverse) is used as the 5'-end primer, relative relation of the gene expression level was collapsed, although these two primers have the same base composition and the same Tm.

Example 2

When V1 (SEQ ID No. 1) and IDT (Saito, H., Kubota, M., Roberts, R. W., Chi, Q., Matsunami, H. (2004), "RTP family members induce functional expression of mammalian odorant receptors", Cell 119(5):679-91, TATAGAATTCGCGGC-CGCTCGCGA (dT)24 (SEQ ID No. 4)) were used in the combination of the primers, the relative relation of the gene expression level was collapsed, although these two primers have 74.5% overall identity of the sequence.

Example 3

When the restriction enzyme cite AscI (GGCGCGCC) of the sequence of V3(dT)24 (SEQ ID No. 3) is changed to the restriction enzyme cite NotI (GCGGCCGC), or V3NotI(dT)24 is combined with V1(dT)24, the relative relation of the gene expression level was collapsed, although these two primers have 76.9% overall identity of the sequence.

It was finally confirmed that oriented amplification is efficiently performed while errors are suppressed by using a primer set having about 80% of identity of the overall sequence.

The first and second primers to be used preferably have higher Tm than the primers used in usual PCR. Using the primers having higher Tm than primers used in usual PCR permits the annealing temperature to come close to Tm of the primer, and non-specific annealing may be suppressed.

Since the annealing temperature is typically 55° C., Tm of the primer used in usual PCR is 60° C. However, the annealing temperature of the primer used in the present invention is from 60° C. or more to less than 90° C., preferably about 70° C., and most preferably 67° C.

(d) PCR Amplification

Next, the first primer is added, and PCR amplification is performed.

An appropriate PCR cycle number is to be determined for efficiently amplifying DNA while the systematic error is suppressed. In an experiment, 4 to 30 cycles of PCR was performed using RNA derived from ES cells that had been diluted to a single cell level as a starting material, and the relative amount of several gene products having several to hundreds times of relative expression level were compared. The maximum cycle number for efficient amplification while the relative relations are maintained was determined to be 24 cycles from the results. However, since the cycle number may be varied depending on the solvent, temperature and primers used in PCR, the PCR amplification cycle number in the present invention is from 10 to 30 cycles, preferably about 20 cycles.

Non-specific annealing can be suppressed in step (d) by permitting the annealing temperature in PCR amplification to come close to Tm of the primer used. For example, when a primer pair comprising the nucleic acid molecule having the nucleotide sequence represented by SEQ ID No. 1 and the nucleic acid molecule having the nucleotide sequence represented by SEQ ID No. 2 is used, the annealing temperature is from 60° C. or more to less than 90° C., preferably about 70° C., and most preferably 67° C.

Primary strand cDNA derived from the same starting sample is divided into a plurality of tubes, for example from 3 to 10 tubes, preferably about 4 tubes, in step (d), and cDNA in each tube is subjected to a PCR reaction, and the reaction products in respective tubes are preferably mixed. This permits the random errors to be averaged to enable the error to be remarkably suppressed.

(e) PCR Amplification Using Third Primer

Third primer is a primer in which, a promoter region is linked to the 5'-end of the additional nucleotide sequence X or Y of the nucleotide sequence in the first primer or second primer.

Accordingly, the primer set used in this step is selected from any one of:

(1) a primer set comprising a combination of a third primer comprising the additional nucleotide sequence X and a promoter sequence linked to a 5'-end of the nucleotide sequence X, and the second primer, or (2) a primer set comprising a combination of the third primer comprising the additional nucleotide sequence Y and a promoter sequence linked to a 5'-end of the nucleotide sequence Y, and the first primer.

While the promoter region is not particularly limited so long as the region is recognizable with RNA polymerase, it is preferably T7 promoter region, T3 promoter region or SP6 promoter region. Specifically, a nucleic acid molecule having the nucleotide sequence represented by SEQ ID No. 3 is used.

PCR amplification is performed from 4 to 10 cycles, preferably 5 cycles, using the primer set (1) or (2). At least 3 cycles is necessary for securing a sufficient number of amplification products including the promoter region.

The annealing temperature is the same as described in (d).

A group of nucleic acids comprising the amplification products that retain the relative relation of the gene expression level in the biological sample may be prepared by the steps from (a) to (e). In another aspect, the present invention provides a group of nucleic acids comprising the amplification products that retain the relative relation of the gene expression level in the biological sample may be prepared by the steps from (a) to (e), wherein the amplification products has an approximately uniform length. The phrase "has an approximately uniform length" as used herein refers to obtaining amplification products having a uniform length with respect to mRNAs having a long total length, and does not exclude the presence of the amplification products having a short length. The amplification product in the group of nucleic acids of the present invention has directionality that enables the 3-end and 5'-end to be discriminated from each other.

While the group of nucleic acids of the present invention obtained by the above-mentioned steps is useful as a sample to be applied to quantitative microarray analysis or as a sample for determining the sequence, the amplification product obtained by the method of the present invention is a mixture of cDNA (a group of a part of DNAs mainly having a length of about 500 bp or less) derived from mRNA and by-product DNA (a group of DNAs mainly having a length of about 200 bp or less). When in vitro transcription reactions are performed by addition of promoter regions while such by-products exists, RNAs using the by-products as a template are synthesized in the next step (f). This may adversely affects the hybridization experiment on the microarray. In other words, it is difficult to measure the necessary amount of the target RNA when the by-products are mingled, because it is difficult to distinguish the by-product from "correct" products in quantification of the amount of RNAs. Accordingly, it is necessary to remove the by-product DNAs in the amplification product depending on the use of the amplification product (for example, when the amplification products are converted into RNAs by in vitro transcription reaction for applying to a series of oligonucleotide microarray GeneChip manufactured by Affymetrix, Inc.).

While any methods known in the art such as gel filtration and gel electrophoresis may be used in the step for removing the by-product DNA, it is preferable to remove the by-product DNA by gel electrophoresis. The reason is that gel electrophoresis is simple in operation, exhibits good recovery yield, has high size separation ability, and is inexpensive. Since the length of the by-product DNA is usually 300 bp or less, DNAs with a length of, for example, 200 bp or less may be removed. While the timing of removal of the by-product DNA may be either before or after addition of the promoter region, the timing is preferably after addition of the promoter region in terms of purification efficiency and safety of operation (prevention of loss of cDNA as a sample), because there are a lot of amplified cDNAs after addition of the promoter region.

The inventors of the present invention have found that the relative gene expression level of RNAs as transcription products changes with a certain frequency when the in vitro transcription reaction is performed using the group from which by-product DNAs are removed as described above as a template. It has been found for solving the problem that the relative gene expression level in the transcription product RNA is perfectly maintained when PCR is performed again after the step for removing the by-product DNA and the amplification product is used as a template for the in vitro transcription reaction (see Example 2). While the PCR condition is not particularly limited so long as the desired DNA sequence is amplified, the preferable PCR condition is similar to that in the promoter sequence addition reaction in step (e). While the number of the PCR cycle is also not limited, several cycles are usually sufficient. The number of cycles is preferably reduced for making the risk of change of the relative gene expression level by PCR small, applying only one cycle of PCR may be effective.

The removing step of the by-product DNA and the PCR amplification step thereafter are applicable to the method for preparing the group of nucleic acids comprising the amplification product that maintains a relative relation of the gene expression level in the biological sample, and the following nucleic acid amplification method of the present invention, the preparation method of a nucleic acid library that retains a relative relation of the gene expression level the biological sample, and the kit of the present invention.

(f) Conversion of the Group of Nucleic Acids of the Present Invention into the Group of Nucleic Acids Comprising RNAs A group of nucleic acids comprising labeled RNAs can be prepared by applying RNA polymerase and labeled nucleotide triphosphate to the group of nucleic acids of the present invention obtained in steps (a) to (e). The group of labeled nucleic acids may be applied to a series of oligonucleotide microarray GeneChip (manufactured by Affymetrix, Inc.)

that is able to simultaneously measure the expression levels of plural genes, and is currently being a main stream.

(2) Method for Amplification of Nucleotide Sequence

In another aspect, the present invention provides an method for amplification of the nucleotide sequence including steps (a) to (e) in the method for preparing the group of nucleic acids of the present invention. Preferably, the nucleotide sequence contains an amplification product that retains a relative relation of the gene expression level in the biological sample.

(3) Method for Preparing a Nucleic Acid Library that Retains a Relative Relation of the Gene Expression Level in the Biological Sample In a further different aspect, the present invention provides a method for preparing a nucleic acid library that retains a relative relation of the gene expression level in the biological sample including steps (a) to (e) in the method for preparing the group of nucleic acids of the present invention.

The cDNA library prepared by the method of the present invention retains a relative relation of the gene expression level in the biological sample. Tens of thousands of colonies corresponding to each transformant may be formed by transforming E. coli with plasmids in which the cDNA library is cloned, and by cultivating the cells on a culture medium. Then, the sequences of each plasmid are determined by picking up the colonies, and are arranged in a database. The gene having a high expression frequency may appear on the database as quite the same sequence corresponding to the expressed gene with a frequency corresponding to the expression frequency. Accordingly, the relative relation of the gene expression level in the biological sample may be theoretically determined without using the microarray by counting the frequency as described above. In other words, the relative relation of the gene expression level may determined, though genome information be known or unknown, by investigating the frequency of the same sequence by a comprehensive sequence analysis after preparing the cDNA library of the present invention. The database on the library thus prepared is referred to an expression sequence tag [EST] database. While some known EST databases may contain unknown directions of 5'- and 3'-ends of EST, the direction is clearly indicated in the library prepared by the method of the present invention. [Directional] EST library databases that retain the relative relation of the gene expression level with good reproducibility are quite effective in that the relative gene expression level is shown at a single cell level even in biological species to which the microarray is hardly applicable, or in most of biological species in which total genome sequences have not been elucidated yet. An analysis taking the difference among individuals such as genetic polymorphism into consideration may be possible in a single cell level with respect to biological species whose total genome has been known.

(4) Kit for Preparing a Group of cDNAs to be Applied to Microarray

In a further different aspect, the present invention provides a kit for preparing a group of cDNAs to be applied to a microarray.

The kit of the present invention includes:

(a) a first primer comprising a poly(T) sequence and an additional nucleotide sequence X thereto, for preparing a primary strain cDNA from mRNAs isolated from a biological sample;

(b) a reagent for inactivating the first primer;

(c) a second primer comprising poly(T) sequence and an arbitrary nucleotide sequence Y for a double-stranded DNA, wherein the nucleotide sequences X and Y in the first and second primers, respectively, have different sequences from each other; and (d) a primer set (1) or (2) below:

(1) a primer set comprising a third primer comprising the additional nucleotide sequence X and a promoter sequence linked to the 5'-end of the sequence X and the second primer; and (2) a primer set comprising a third primer comprising the additional nucleotide sequence Y and a promoter sequence linked to the 5'-end of the sequence X and the first primer.

The kit of the present invention may contain other reagents for amplifying nucleic acids, or may further contain primers for a control experiment.

Examples of the constituting elements contained in the kit are as follows: all the reagents shown in following examples; Spike RNA; RNA derived from ES cells (for control experiments); cDNA amplification primer (V18dT]24, V3-[dT}24, T7V1); DNA purification kit (Quiagen); and PCR primers for real time PCR for control experiments (gene specific primers Gapdh, Oct4, Nanog, Sox2, Ezh 2, Yyl, Eras and Tiar).

The kit of the present invention preferably used for preparation of a group of cDNAs comprising amplification products that retain relative relations of gene expression level in the biological sample.

The kit of the present invention may be used for implementing the method for preparing a group of nucleic acids comprising an amplification product that retains a relative relation of gene expression level in the biological sample of the present invention, the nucleic acid method for amplification and the method for preparing a nucleic acid library that retains a relative relation of gene expression level in the biological sample.

While the present invention is described in more detail with reference to Examples, the present invention is not limited to these Examples.

Each buffer solution used in Examples was prepared with reference to Saito, H., Kubota, M., Roberts, R. W., Chi, Q. and Matsunami, H. (2204), "RTP family members induce functional expression of mammalian odorant receptors", Cell 119 (5): 679-91, and has the following compositions.

TABLE 1

| (1)cell lysis buffer solution (µL) | |
|---|---|
| 10 × PCR buffer solution II (contains no $MgCl_2$), (Applied Biosystems) | 10.0 |
| $MgCl_2$ (Applied Biosystems), 25 mM | 6.0 |
| NP 40 (Nakalai), 5% | 10.0 |
| DTT (Invitrogen), 0.1M | 5.0 |
| Prime RNase Inhibitor (trade name) (Eppendorf), 30 U/µL | 1.0 |
| RNAgurad RNase Inhibitor (trade name) (Amersham), 31.2 U/µL | 1.0 |
| Primer V1 $(dT)_{24}$, 10 ng/µL | 2.0 |
| dNTP (dATP, dCTP, dGTP and dTTP), 25 mM each | 2.0 |
| Spike RNA mixture (Lys 1000, Dap 100, Phe 20 and Thr 5 copies/µL) | 21.0 |
| DDW (twice-distilled deionized water) (Gibco) | 42.0 |

TABLE 1-continued

| | |
|---|---:|
| Final volume (2)RT mixture (µL) | 100.0 |
| Superscript III (trade name) (Invitrogen) 200 U/µL | 6.0 |
| RNAguard RNase Inhibitor (trade name) (Amersham) 31.2 U/µL | 1.0 |
| T4 gene 32 proteins (trade name) (Roche) 6 µg/µL | 2.0 |
| Final volume (3)Exonuclease I mixture (µL) | 9.0 |
| 10 × Exonuclease I buffer solution (Takara) | 3.0 |
| DDW (twice-distilled deionized water) (Gibco) | 24.0 |
| Exonuclease I (Takara) 5 U/µL | 3.0 |
| Final volume (4)TdT mixture (µL) | 30.0 |
| 10 × PCR buffer solution II (contain no $MgCl_2$) (Applied Biosystems) | 12.0 |
| MgCl (Applied Biosystems) 25 mM | 7.2 |
| dATP (Amersham Pharmacia) 100 mM | 3.6 |
| RNaseH (Invitrogen) 2 U/µL | 6.0 |
| Terminal deoxynucleotidyl transferase (TdT), recombinant (Invitrogen) 15 U/µL | 6.0 |
| DDW (twice distilled deionized water) (Gibco) | 85.2 |
| Total volume (5)PCR mixture I (µL) | 120 |
| 10 × Extaq buffer solution | 160.0 |
| dNTP (dATP, dCTP, dGTP and dTTP) 2.5 mM each | 160.0 |
| Primer V3 $(dT)_{24}$ 1 µg/µL | 32.0 |
| Extaq Hot Start Version, 5 U/µL | 16.0 |
| DDW (twice distilled deionized water) (Gibco) | 1232.0 |
| Final volume (6)PCR mixture II (µL) | 1600.0 |
| 10 × Extaq buffer solution | 160.0 |
| dNTP (dATP, dCTP, dGTP and dTTP) 2.5 mM each | 160.0 |
| Primer V1$(dT)_{24}$, 1 µg/µL | 32.0 |
| Extaq Hot Start Version, 5 U/µL | 16.0 |
| DDW (twice distilled deionized water) (Gibco) | 1232.0 |
| Final volume (7)PCR mixture III (µL) | 1600.0 |
| 10 × Extaq buffer solution | 20.0 |
| dNTP (dATP, dCTP, dGTP and dTTP) 2.5 mM each | 20.0 |
| Primer T7-V1, 1 µg/µL | 4.0 |
| Primer V3$(dT)_{24}$, 1 µg/µL | 4.0 |
| Extaq Hot Start Version, 5 U/µL | 2.0 |
| DDW (twice distilled deionized water) (Gibco) | 140.0 |
| Final volume | 190.0 |

The primers used in Table 1 are as follows;

TABLE 2

```
Primer
V1 (dT)24   5'-ATATGGATCCGGCGCGCCGTCGACTTTTTTTTTTTT
(operon)    TTTTTTTTTT-3' (SEQ ID No. 1)

V1 (dT)24   5'-ATATCTCGAGGGCGCGCCGGATCCTTTTTTTTTTTT
(operon)    TTTTTTTTTT-3' (SEQ ID No. 2)

T7-V1       5'-GGCCAGTGAATTGTAATACGACTCACTATAGGGAGGC
(operon)    GGATATGGATCCGGCGCGCCGTCGAC-3' (SEQ ID
            No. 3)
```

Example 1

A. Synthesis and Exponential Amplification of Primary cDNA Chain

Step 1: Addition of Primer V1$(dT)_{24}$

Basal allantoic of mouse early embryo (embryo 6.5 to 8.5 days after fertilization) was cut with a glass capillary to prepare single cells by treating with 0.05% trypsin, and the cells were collected with a mouse pipette.

Twenty cells were collected by one run. A cell lysis buffer solution (4.5 µL, (1) in Table 1) was added to the single cell suspension (<0.5 µL) obtained in a 0.5 ml thin wall PCR tube. The tube was centrifuged with a table-top centrifuge for 15 seconds, and placed on ice. Then, the tube was heated at 70° C. for 90 seconds (bathing), placed on ice for 1 minutes, and centrifuged with a table-top centrifuge followed by placing on ice.

Step 2: Reverse Transcription

RT mixture (0.3 µL, (2) in Table 1) was added to the sample prepared in step 1, and the mixture was allowed to react at 50° C. for 5 minutes (bathing). Then, the reaction mixture was treated at 70° C. for 10 minutes (bathing) to stop the reaction, and the reaction solution was centrifuged with a table-top centrifuge followed by placing on ice for 1 minute.

Step 3: Exonuclease Decomposition

Exonuclease I mixture (1 µL, (3) in Table 1) was added to the sample prepared in step 2, and the sample was treated at 80° C. for 25 minutes (PCR machine). The treatment product obtained was centrifuged followed by placing on ice for 1 minute.

Step 4: Poly(A) Tailing

TdT mix (6 µL, (4) in Table 1) was added to the sample prepared in step 3, and the mixture was allowed to react at 37° C. for 15 minutes (bathing) followed by allowing the reaction to stop by treating at 70° C. for 10 minutes (bathing). The reaction mixture was than centrifuged with a table-top centrifuge followed by placing on ice for 1 minute.

Step 5: Addition of Primer V3$(dT)_{24}$ and PCR Amplification

The reaction product (12 µL, poly(A) tailed reverse transcript) prepared in step 4 was dispensed in four thin-wall 200 µL PCR tube in an amount of 3 µL per tube. PCR mixture I (20 µL, (5) in Table 1) was added to each tube, and one cycle of a DNA elongation reaction was carried out under a condition of 95° C. for 3 minutes, 50° C. for 2 minutes and 72° C. for 3 minutes. The reaction product was allowed to stand on ice for 1 minutes, and was centrifuged for 15 seconds with a table-top centrifuge.

PCR mixture II (20 µL, (6) in Table 1) was added to each tube, and mineral oil was added to each tube. Each tube was subjected to 20 cycles of PCR amplification reaction under a condition of 95° C. for 30 minutes, 67° C. for 1 minute and 72° C. for 3 minutes (additional 6 seconds for each cycle).

Step 6:

The PCR products in respective tubes obtained in step 5 were mixed.

Step 7:

The PCR product was purified with Quiagen PCR purification kit by eluting with 50 µL of EB buffer solution.

B. Addition of T7 Promoter

Step 8:

cDNA (10 µL) prepared in step 7 was dispensed in four thin-wall 300 µL tubes (2.5 µL per one tube) for addition of T7 promoter. PCR mixture III (47.5 µL, (7) in Table 1) was added to each tube followed by addition of mineral oil to each tube. The reaction mixture was subjected to PCR amplification reactions (1 cycle of 95° C. for 5 minutes, 64° C. for 1 minute and 72° C. for 5 minutes and 18 seconds; and 4 cycles of 95°

C. for 5 minutes, 67° C. for 1 minute and 72° C. for 5 minutes and 18 seconds; additional 6 seconds for each cycle).

Step 9:

The PCR products were purified with Quiagen PCR purification kit by eluting with 50 μL of EB buffer solution.

C. Gel Purification

Step 10:

DNA loading buffer solution (7 μL, manufactured by TAKARA Bio Inc.) was added to 35 μL of the product obtained in step 9, and subjected to 2% agarose gel electrophoresis at 100 V for 10 minutes until PBP (bromophenol blue) migrates a distance of about 2 to 3 cm.

Step 11:

Smear DNA (all of 300 bp or more) was cut (about 0.3 to 0.5 g), and was purified with Quiagen gel purification kit.

The final cDNA product gave about 10 μg of non-labeled RNA in 10 μL scale T7 reaction (4 μL is used as a template) for 2 hours using Amicon MEGA Script.

Test Example 1

Comparison Between Usual cDNA Method for Amplification (AL1 Method) and cDNA Method for Amplification (V1V3 Method) of the Present Invention RNA derived from mouse ES cell was diluted to a single cell level (about 10 pg), and cDNA was synthesized and amplified using AL1 method (Non-patent Document 3) and ViV3 method of the present invention. The V1V3 method of the present invention is described in Example 1. In all the experiments, RNA diluted from the same non-amplified RNA (referred to "original RNA" hereinafter) was used for amplification. Six times of independent experiments were carried out for respective methods.

The relative expression level of each gene in the amplified cDNA, or the amount of cDNA after amplification derived from each gene product mRNA, was compared with the relative expression level of each gene in RNA (1 μg) derived from the ES cells that is neither diluted nor amplified, and it was investigated to what extent the deviation from original RNA differs between the AL1 method and VIV3 method.

Thousands to tens of thousands of genes are considered to be expressed in RNAs derived from the ES cells. Representative eight genes (Gapdh, Oct4, Sox2, Ezh2, Yy1, Nanog, Eras and Tiar) were selected among the genes, and the expression levels of the original RNA and amplified cDNA were measured by real time PCR (see: www.takara-bio.co.jp/prt/pdfs/prt1.pdf). The expression level of each gene was normalized using Gapdh to calculate the relative expression level.

Figure 2:
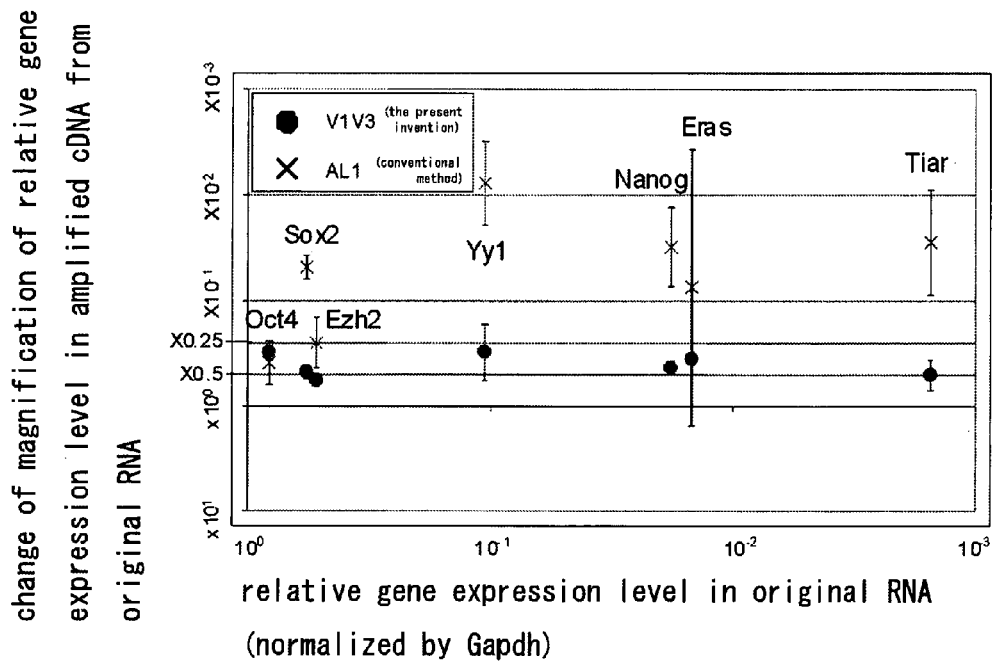
FIG. 2 is a graph for comparing systematic errors and random errors of the gene expression level by the conventional method for amplification of cDNA and by the method for amplification of cDNA of the present invention.

The results obtained are shown in FIG. 2.

In the graph, the relative expression level (the change of magnification from Gapdh, or how much magnification from Gapdh the expression level is) normalized by Gapdh in original RNA was plotted along the horizontal axis. The direction of the axis was determined so that the relative expression level decreases from the left to the right. The expression level of Oct4 was the closest to Gapdh (about 1/1.2 of Gapdh), and the expression level of Tiar was the smallest (about 1/650 of Gapdh). In other words, the gene expression level may be determined in the range of magnification of about 650 by selecting the above-mentioned eight genes.

The change of the relative gene expression level in the group of amplified cDNAs (how much magnification the expression level of the original RNA of each gene normalized by Gapdh is) from the original RNA was plotted along the vertical axis. The deviation is judged larger as the upper or lower shift from a center point ($\times 10^0 = 1$ magnification) is larger. The relative expression level is smaller than the original RNA as the level is plotted upper (estimated to be smaller than the actual level), and the relative expression level is larger than the original RNA as the level is plotted lower (estimated to be larger than the actual level). The marks (●) and (x) denote the average values of deviations of the relative gene expression level from the original mRNA in the group of cDNAs amplified by the V1V3 method and AL1 method, respectively. The bar denotes the standard deviation in each method and each gene expression level.

FIG. 2 indicates the magnitude of the distortion of the relative gene expression level caused in the DNA amplification process by the AL1 method and V1V3 method. In the graph, the systematic errors (errors generated with reproducibility) are indicated by marks (●) and (x), while the magnitude of the random errors (the magnitude of variations among the experiments) is indicated by bars.

In the V1V3 method (●), the deviations from the original mRNA fall within a range of magnification from 0.5 (one half) to 0.24 s (one fourth). On the other hand, the shifts from the original mRNA is far larger in the AL1 method (x), and many genes are plotted in the range from $\times 10^{-1}$ (one tenth) to $10^{-2}$ (one hundredth).

Notice that the length of the bar of each gene, then it is shown that V1V3 method falls within a far smaller width than the AL1 method.

These results indicated that the VIV3 method is far improved in the systematic error and random error that the AL1 method is.

Test Example 2

Comparison of Signal Intensities on the Microarray Between the Original RNA and the Group of Amplified cDNAs RNAs (5 μg, about $5 \times 10^5$ cells) derived from the original ES cells were used for GeneChip microarray analysis manufactured by Affymetrix, Inc. The RNAs derived from the ES cells were diluted to a single cell level (about 10 pg), and were also subjected to GeneChip microarray analysis using the group of cDNAs amplified by the V1V3 method of the present invention.

Figure 3:
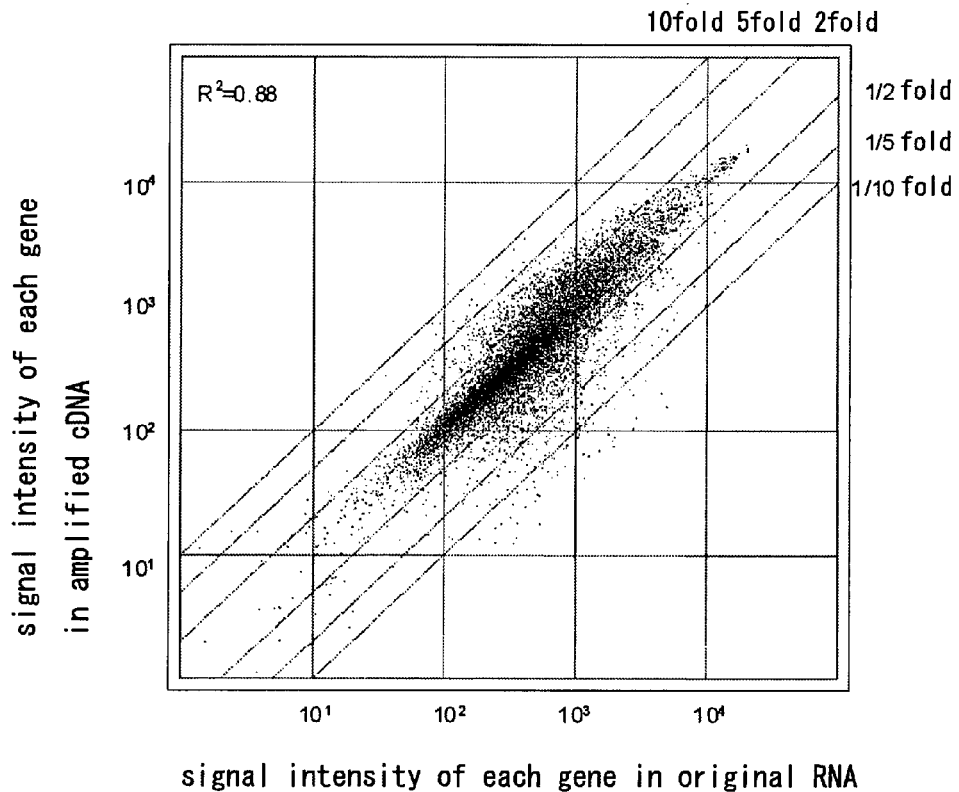
FIG. 3 is a graph for comparing signal intensities on a microarray with respect to the amount of an original RNA and gene expression level by the amplification method of the present invention.

The results obtained are shown in FIG. 3. FIG. 3 indicates to what extent the relative relation of the original gene expression level is retained in the cDNA amplification process.

In FIG. 3, the signal intensity of each gene in the original RNA is plotted in the horizontal axis, and the signal intensity in each gene in the group of amplified cDNAs is plotted in the vertical axis. The lines corresponding to magnification of 2, 5, 10, ½, ⅕ and 1/10 of the changes of magnification from the original mRNA are shown on the graph.

FIG. 3 shows that 90% or more of total genes falls within the range of magnification from ½ to 2. The $R^2$ value between the signal intensities of the group of amplified cDNAs and original RNA was 0.88 ($R^2$ value=square of the correlation coefficient R). These results show that amplification by the V1V3 method does not largely distort the relative relation of gene expression. These results favorably fit the results of the measurement by real time PCR experiment with respect to eight representative genes.

Test Example 3

Comparison of signal intensities between two groups of independently amplified DNAs RNAs derived from ES cells were diluted to a single cell level, two of the diluted ES cells are selected and independently amplified in different tubes to obtain cDNA group #1 and cDNA group #2. These two groups were subjected to GeneChip microarray analysis.

Figure 4:
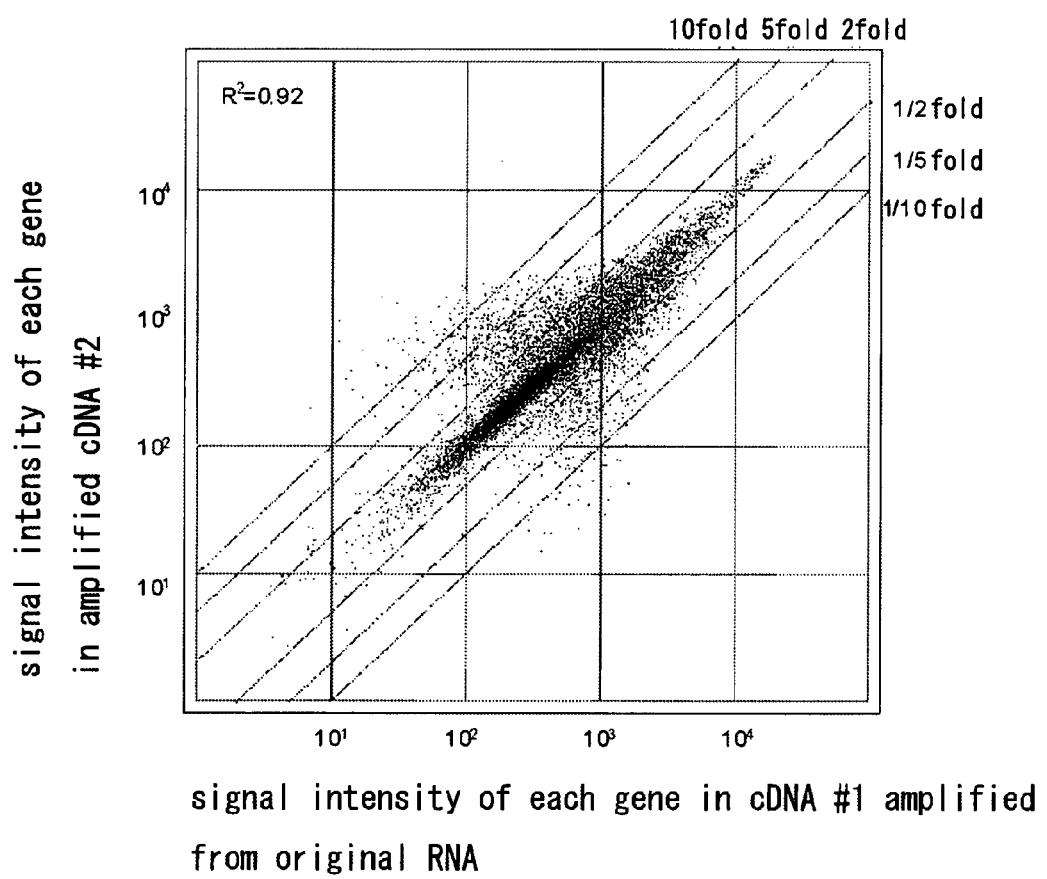
FIG. 4 is a graph for comparing signal intensities on the microarray with respect to two gene expression levels independently amplified by the amplification method of the present invention.

The results obtained are shown in FIG. 4. FIG. 4 indicates that to what extent reproducibility of cDNA amplification is.

In FIG. 4, signal intensities of amplified cDNA group #1 are plotted along the horizontal axis and signal intensities of amplified cDNA group #2 are plotted along the vertical axis. Signal intensities of 90% or more of the total genes fall within the range of magnification from ½ to 2. The $R^2$ value between signal intensities of two cDNA groups was 0.92.

Plots of genes are concentrated in the vicinity of a diagonal line, and the proportion of the genes with a change of magnification of 2 or less was 90% or more. This means that genes are amplified with good reproducibility by the V1V3 method.

Test Example 4

Correspondence Between the Copy Number of Gene Products and Signal Intensity on the Microarray An example called as a "Spike method" was performed for correlating the signal intensity on the microarray with the copy number of mRNA.

In the Spike method, RNAs (Spike RNAs) that do not exist on the mouse genome are added as positive controls in the reaction system including synthesis, amplification and labeling of cDNA. Since probes for targeting genes (lys, dap, phe, thr and trp) derived from *Bacillus subtilis* are provided in Affymetrix GeneChip, these genes may be used as Spike RNAs. Since these genes derived from *B. subtilis* as a prokaryotic bacterium has no poly(A) at the 3'-end, the gene is not directly amplified in our cDNA method for amplification. Therefore, poly dA is added to 3'-ends of lys, dap, phe, thr and trp genes, and artificial genes that are made to encode mRNAs of pseudo-eukaryotic organism are cloned in the plasmid. mRNAs are synthesized using these artificial genes as templates, and are preserved after purification. How much these mRNAs are added to the cDNA amplification reaction system may be freely determined by those in charge of the experiment so that the copy number of RNAs added may be correlated with the signal intensity derived from the RNAs.

Lys, Dap, Phe and Thr RNAs having poly(A) artificially added to each 3'-terminal were added so that copy numbers are 1000, 100, 20 and 5 per one cell, and cDNA was synthesized and amplified using these RNAs together with the RNA derived from ES cells.

Figure 5:
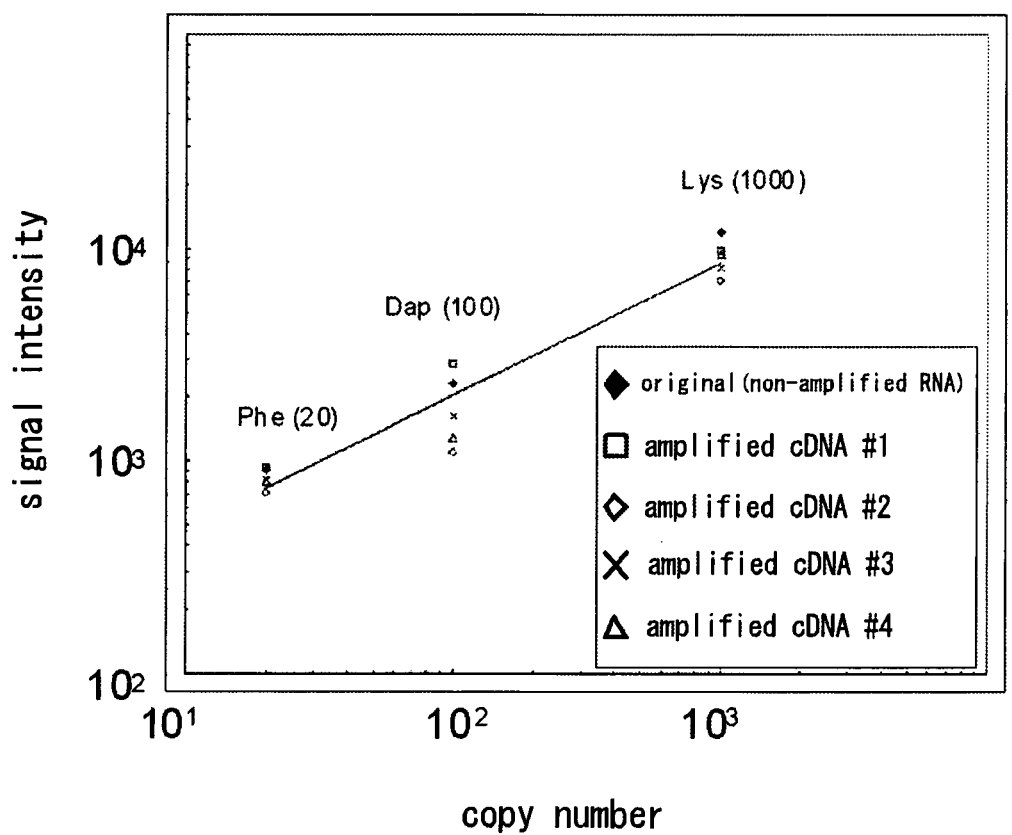
FIG. 5 is a graph showing a relation between the copy number of the gene product by the amplification method of the present invention and signal intensities on the microarray.

The results obtained are shown in FIG. 5.

In the graph, the copy number added is plotted along the horizontal axis and the signal intensity is plotted along the vertical axis. The black rhomboid denotes non-amplified Spike RNA (for 5×10⁵ cells) added to the original RNA (5 μg, about 5×10⁵ cells). The white square, rhomboid, triangle and cross denotes Spike RNAs added to RNAs derived from ES cells diluted to a single cell level. These Spike RNAs are added in an amount for one cell. While Lys, Dap and Phe RNAs were amplified with good reproducibility, amplification of Thr RNA was poor in reproducibility. The R2 factor between the copy number of Lys, Dap or Phe RNA and signal intensity was 0.93. The results in FIG. 5 show that correlation between the copy number and signal intensity is good in the range from 20 copies to 100 copies. This indicates that the amplification method of the present invention has quantitativity enough for estimating the copy number of mRNA from the signal intensity at least for mRNA of 20 copies or more.

Example 2

The product (μg) obtained in step 9 in Example 1 was fractionated into sizes by 2% agarose gel electrophoresis, and each band was visualized by ethidium bromide staining. The portion of the gel containing DNAs with a size of 300 bp or less was cut with a commercially available razor blade, and DNA was extracted form gel fragments using Quiagen gel DNA extraction kit (trade name: Qiaquick GelExtraction Kit).

No by-products were found at all in the cDNA sequence analysis of randomly selected 40 cDNAs with respect to the DNA group from which by-products were removed as described above. No changes of relative expression levels before and after gel purification were also observed (FIG. 6(*a*)).

The DNAs extracted from gel fragments were subjected to 1 cycle PCR using the same compositions of the buffer solution, substrate and enzyme as in the promoter sequence addition reaction. The composition of the reaction solution was as follows:

| | |
|---|---|
| 10 × ExTaq buffer (TAKARA Bio Inc.) | 20.0 μL |
| 2.5 mM each dNTP (dATP, dCTP, dGTP, dTTP: TAKARA Bio Inc.) | 20.0 μL |
| H₂O | 141.2 μL |
| cDNA (DNA after removing by-products) | 8.8 μL |
| ExTaq Hot Start version (TAKARA Bio Inc.) | 2.0 μL |
| Total | 200.0 μL |

The temperature condition of PCR was: 95° C. for 5 minutes, 30 seconds, 67° C. for 1 minute, and 72° C. for 16 minutes in this order.

Figure 6:
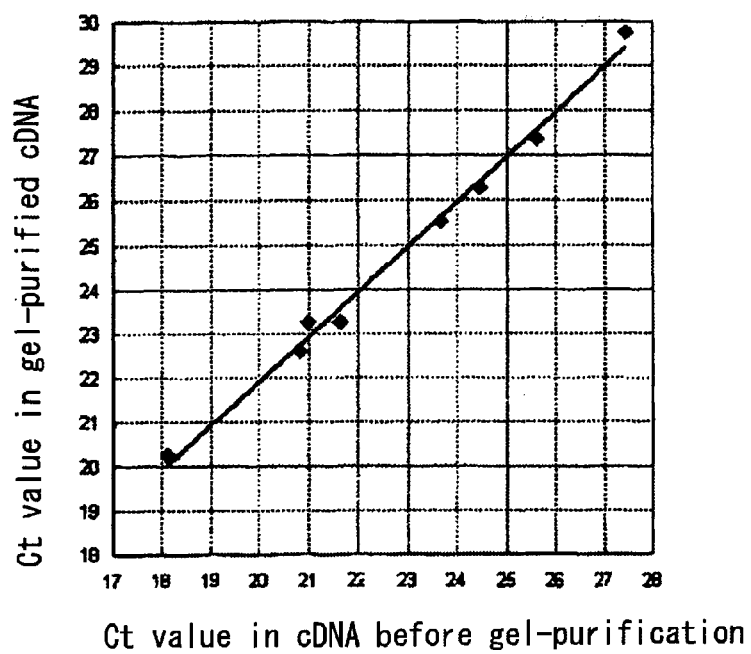
FIG. 6(a) is a graph showing that the relative gene expression level is maintained before and after purification (gel purification) by gel electrophoresis. The relative gene expression level was measured using real time PCR manufactured by Applied Biosystems. The vertical axis and horizontal axis denote the relative gene expression levels before and after gel purification, respectively. The gene expression level is shown by cycles of threshold (Ct values).
FIG. 6(b) is a graph showing changes of the relative gene expression levels after the in vitro transcription reaction. The white squares show the results of the direct in vitro transcription reaction immediately after purification, while black squares show the results of the in vitro transcription reaction after 1 cycle of PCR after gel purification. The horizontal axis denotes the relative gene expression revel of DNA after gel purification, and the vertical axis denotes the relative gene expression level of RNA after the in vitro transcription reaction. The relative gene expression level of RNA is measured by real time PCR after converting RNA into DNA by the reverse transcription reaction. Maintenance of the relative gene expression level was remarkably improved by 1 cycle of PCR.
Figure 6:
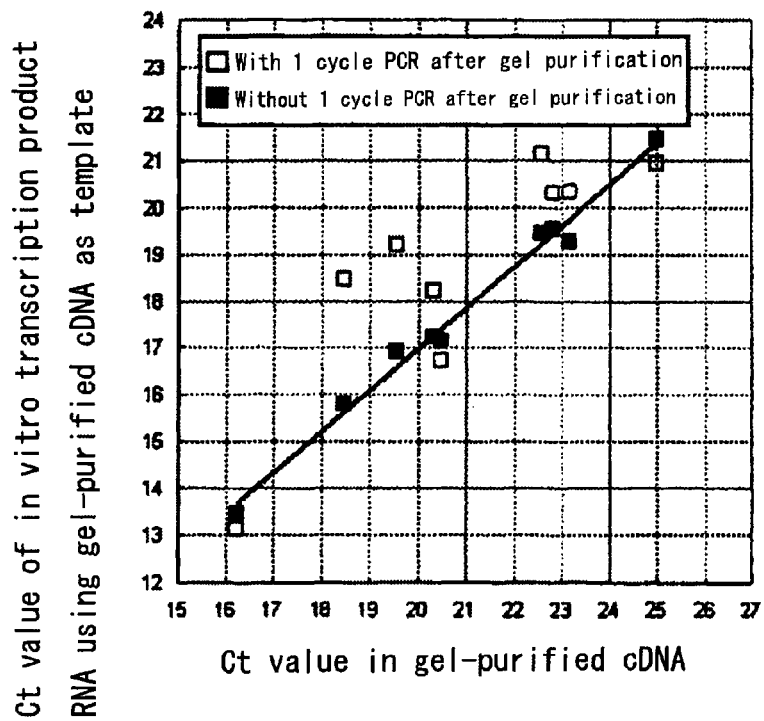

It was shown that the relative gene expression level was completely maintained in the transcription product RNA (FIG. 6(*b*)). The RNA series thus obtained is quite favorable for use in, for example, a series of oligonucleotide microarray GeneChip manufactured by Affymetrix, Inc.

INDUSTRIAL APPLICABILITY

The present invention is applicable in a biochemical research, medical, food industry or substance production field.

What is claimed is:

1. A method for preparing a group of nucleic acids comprising amplification products retaining a relative relation of each gene expression level in a biological sample, comprising:
   (a) preparing a primary cDNA chain by reverse transcription using mRNA isolated from a biological sample as a template and using a first primer comprising a poly(T) sequence and an additional nucleotide sequence X thereto;
   (b) inactivating the remaining first primer after the reaction in (a);
   (c) subjecting the primary cDNA chain obtained in (a) to a poly(A) tailing reaction followed by preparing a secondary double-stranded DNA chain using the poly(A) tailing reaction product as a template and using a second primer comprising poly(T) sequence and an additional nucleotide sequence Y thereto, wherein the nucleotide sequences X and Y in the first and second primers, respectively, have different sequences from each other;
   (d) adding the first primer, and performing PCR amplification between the first primer and the second primer; and
   (e) performing PCR amplification using primer set (1) or (2) below,
       (1) a primer set comprising a combination of a third primer comprising the additional nucleotide sequence X and a promoter sequence linked to a 5'-end of the nucleotide sequence X, and the second primer, or
       (2) a primer set comprising a combination of the third primer comprising the additional nucleotide sequence Y and a promoter sequence linked to a 5'-end of the nucleotide sequence Y, and the first primer
   wherein the nucleotide sequences X and Y do not contain promoter sequences that are recognized by RNA polymerase.

2. The method according to claim 1, wherein the length of the primary cDNA chain prepared in (a) is almost uniform.

3. The method according to claim 1, wherein the remaining first primer in (b) is inactivated by decomposition with exonuclease I.

4. The method according to claim 1, wherein the PCR amplification in (d) is performed for 10 to 30 cycles.

5. The method according to claim 1, wherein the PCR amplification in (e) is performed for 4 to 10 cycles.

6. The method according to claim 1 further comprising (f) preparing a group of nucleic acids comprising labeled RNA by applying RNA polymerase and labeled nucleotide triphosphate to the group of nucleic acids obtained in (e).

7. The method according to claim 1, wherein, in (a), a reverse transcription reaction is performed for 5 to 10 minutes.

8. The method according to claim 1 wherein, in (d), the double-stranded secondary strain DNA obtained in (c) is divided into from 3 to 10 portions followed by PCR amplification of each portion, and each amplification, product is collected together.

9. The method according to claim 1, wherein, in (d) and (e), an annealing temperature for PCR amplification is made to come close to Tm of the primer.

10. The method according to claim 1 comprising removing by-product DNAs in the amplification product after addition of a primer sequence in (e) followed by the PCR amplification.

11. The method according to claim 1, wherein the biological sample is cells of eukaryotic organisms.

12. The method according to claim 11, wherein the biological sample contains from one to several cells.

13. The method according to claim 12, wherein the biological sample contains one cell.

14. The method according to claim 1, wherein the first primer comprises a nucleotide sequence represented by SEQ ID No. 1, the second primer comprises a nucleotide sequence represented by SEQ ID No. 2, and the third primer comprises a nucleotide sequence represented by SEQ ID No. 3.

15. A quantitative microarray analysis method in which the group of nucleic acids comprising the amplification products prepared by the method according to claim 1 and retaining a relative relation of the gene expression level in the biological sample are applied to a microarray, wherein the length of the amplification products is almost uniform.

16. A method for preparing a nucleic acid library retaining a relative relation of each gene expression level in the biological sample, comprising
  (a) preparing a primary cDNA chain by reverse transcription using mRNA isolated from a biological sample as a template and using a first primer comprising a poly(T) sequence and an additional nucleotide sequence X thereto;
  (b) inactivating the remaining first primer after the reaction in (a);
  (c) subjecting the primary cDNA chain obtained in (a) to a poly(A) tailing reaction followed by preparing a secondary double-stranded DNA chain using the poly(A) tailing reaction product as a template and using a second primer comprising poly(T) sequence and an additional nucleotide sequence Y thereto, wherein the nucleotide sequences X and Y in the first and second primers, respectively, have different sequences from each other;
  (d) adding the first primer, and performing PCR amplification between the first primer and the second primer; and
  (e) performing PCR amplification using a primer set (1) or (2) below:
    (1) a primer set comprising a combination of a third primer comprising the additional nucleotide sequence X and a promoter sequence linked to a 5'-end of the nucleotide sequence X, and the second primer, or
    (2) a primer set comprising a combination of the third primer comprising the additional nucleotide sequence Y and a promoter sequence linked to a 5'-end of the nucleotide sequence Y, and the first primer
wherein the nucleotide sequences X and Y do not contain promoter sequences that are recognized by RNA polymerase.

17. The method according to claim 16 further comprising removing by-product DNAs in the amplification product after addition of a primer sequence in (e) followed by PCR amplification.

* * * * *